(12) United States Patent
Lu et al.

(10) Patent No.: US 6,300,476 B1
(45) Date of Patent: Oct. 9, 2001

(54) ANTI-PEPTIDE ANTIBODY AGAINST HUMAN CYTOCHROME P450 3A4

(75) Inventors: Anthony Y. H. Lu, Westfield; Regina W. Wang, Montvale, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/057,897

(22) Filed: Apr. 9, 1998

Related U.S. Application Data

(60) Provisional application No. 60/043,230, filed on Apr. 10, 1997, now abandoned.

(51) Int. Cl.$^7$ .................................................... C07K 16/00
(52) U.S. Cl. .............................. 530/387.1; 530/387.9; 530/389.1; 530/389.2
(58) Field of Search ........................... 530/387.1, 387.9, 530/389.1, 389.2

(56) References Cited

FOREIGN PATENT DOCUMENTS

| | | |
|---|---|---|
| 0 644 267 A2 | 7/1994 | (EP) . |
| 08027197 * | 1/1996 | (JP) . |

OTHER PUBLICATIONS

Bork et al. "Charaterization of mRNA Species Related to Human Liver Cytochrome P–450 Nifedipine Oxidase and the Regulation of Catalytic Activity", Jour. of Biol. Chem. vol. 264, No. 2, Issue of 1/16; pp 910–919, 1989.

Komori et al. "Cytochrome P–450 in Human Liver Microsomes: High–Performance Liquid Chromatographic Isolation of Three Forms and Their Characterization"; J. Biochem, 104, 912–916 (1988).

Watkins et al. "Identification of an inducible form of cytochrome P–450 in human liver", Proc. Natl. acad. Sci USA, vol. 82, pp 6310–6314, Sep. 1985.

Leeder et al. "Epitope Mapping Studies with Human Anti–Cytochrome P450 3A Antibodies", Molecular Pharma. vol. 49, pp 234–243 (1996).

Belloc et al. "Human cytochromes P450 expressed in *Escherichia coli*: production of specific antibodies"; Toxocology 106; pp 207–219 (1996).

Soucek et al. "Identification of a Common Cytochrome P450 Epitope near the Conserved Heme–Binding Peptide with Antibodies Raised aganist Recombinant Cytochrome P450 Family 2 Proteins", Biochemistry 1995, 34 pp 16013–16021.

Lewis et al. "Three–dimensional models of human and other mammalian microsomal P450s constructed from an alignment with P450102 (P450bm3)", Xenobiotica 1995, vol. 25, No. 4 pp 333–366.

Edwards et al. "Identification and Location of alpha–Helices in Mammalian Cytochromes P450", Biochemistry 1989, 28, pp 3762–3770.

Gotoh et al. "Substrate Recognition Sites in Cytochrome P450 Family 2 (CYP2) Proteins Inferred from Comparative Analyses of Amino Acid and Coding Nucleotide Sequences", Jour. of Bio. Chem., vol. 267, No. Issue of 1/5, pp 83–90 91992).

Edwards et al. "An inhibitory monoclonal anti–protein antibody and an anti–peptide antibody share an epitope on rat cytochrome P–450 enzymes CYP1A1 and CYP1A2", Biochimica et Biophysica Acta, 1161 (1993) pp 38–46.

Edwards et al. "Identification of the Epitope of an Anti–Peptide Antibody which Binds to CYP1A2 in Many Species Including Man", Biochemical Pharmacology, vol. 46, No. 2 pp 213–220 (1993).

Edwards et al. "Antibodies to a Synthetic Peptide that React Specifically With a Common Surface Region on Two Hydrocarbon–Inducible Isoenzymes of Cytochrome P–450 in the Rat", Biochemical Pharmacology, vol. 37, No. 19, pp 3735–3741 (1968).

Sanghera et al. "Immunocytochemical Distribution of Aromatase Cytochrome P450 in the Rat Brain using Peptide Generated Polyclonal Antibodies", Endocrinology, vol. 129, No. 6 pp 2834–2844.

Manns et al. "Patients with Type II Autoimmune Hepatitis Express Functionally Intact Cytochrome P–450 db 1 that is Inhibited LKM–1 Autoantibodies In Vito but not In Vivo", Hepatology, vol. 12, No. 1, 1990, 127–132.

Manns, et al. "LKM–1 Autoantibodies Recognize a Short Linear Sequence in P450IID6, a Cytochrome P–450 Monoxoygenase", J. Clin. Invest. vol. 88, pp 1370–1378 (Oct. 1991).

* cited by examiner

*Primary Examiner*—Susan Ungar
(74) *Attorney, Agent, or Firm*—Anna L. Cocuzzo; Jack L. Tribble

(57) ABSTRACT

Anti-peptide antibody raised against a portion of human cytochrome P450 3A4 is disclosed. A particular anti-peptide antibody was raised against a 21-amino acid peptide corresponding to residues 253–273 of human cytochrome P450 3A4. High titer antibodies were produced by rabbits immunized with this peptide as judged by ELISA. This anti-peptide antibody is specific for human CYP3A4 and exhibited greater than 90–95% inhibition of testosterone 6β-hydroxylation, while other cytochrome P450-mediated reactions in human liver microsomes were not inhibited. An inhibitory epitope has been mapped within amino acids 261–267 of human CYP3A4.

2 Claims, 12 Drawing Sheets

| 1A2 | 2C9 | 2D6 | 2E1 | 3A4 | 1A1 | 2A6 | 2B6 | 2F1 |
|---|---|---|---|---|---|---|---|---|
|   |   |   |   | — |   |   |   |   |

FIG.2A

| UM622 | UM621 | UC9402 | UC9410 | UC9411 | UC9504 | JS |
|---|---|---|---|---|---|---|
| — | — | ● | ● | ● | ● | ● |

FIG.2B

SEQUENCE LISTING

```
(1) GENERAL INFORMATION:

(iii) NUMBER OF SEQUENCES: 36

(2) INFORMATION FOR SEQ ID NO:1:

(i) SEQUENCE CHARACTERISTICS:
          (A) LENGTH: 21 amino acids
          (B) TYPE: amino acid
          (C) STRANDEDNESS: single
```

(D) TOPOLOGY: linear (ii) MOLECULE TYPE: peptide (xi) SEQUENCE DESCRIPTION: SEQ ID NO:1:

Val Lys Arg Met Lys Glu Ser Arg Leu Glu Asp Thr Gln Lys His Arg
1               5                  10                  15

Val Asp Phe Leu Gln
            20

(2) INFORMATION FOR SEQ ID NO:2:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Cys Val Lys Arg Met Lys Glu Ser Arg Leu Glu Asp Thr Gln Lys His
1               5                  10                  15

Arg Val Asp Phe Leu Gln
            20

(2) INFORMATION FOR SEQ ID NO:3:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Arg Leu Glu Asp Thr Gln Lys His Arg
1               5

(2) INFORMATION FOR SEQ ID NO:4:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Cys Arg Leu Glu Asp Thr Gln Lys His Arg
1               5                  10

(2) INFORMATION FOR SEQ ID NO:5:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Val Lys Arg Met Lys Glu Ser Arg Leu Glu Asp Thr Gln Lys His Arg
1               5                  10                  15

Val Asp (2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Val Lys Arg Met Lys Glu Ser Arg Leu Glu Asp Thr Gln Lys His
1               5                   10                  15

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Leu Glu Asp Thr Gln Lys His Arg Val Asp
1               5                   10

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Lys Glu Ser Arg Leu Glu Asp Thr Gln Lys His
1               5                   10

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Leu Glu Asp Thr Gln Lys His
1               5

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Glu Asp Thr Gln Lys
1               5
```

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Cys Val Lys Arg Met Lys Glu Ser Arg Leu Glu Asp Thr Gln Lys His
1               5                   10                  15
Arg Val Asp
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Cys Val Lys Arg Met Lys Glu Ser Arg Leu Glu Asp Thr Gln Lys His
1               5                   10                  15
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Cys Leu Glu Asp Thr Gln Lys His Arg Val Asp
1               5                   10
```

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Cys Lys Glu Ser Arg Leu Glu Asp Thr Gln Lys His
1               5                   10
```

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Cys Leu Glu Asp Thr Gln Lys His
1               5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Cys Glu Asp Thr Gln Lys His
1               5

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Val Lys Arg Met Lys Glu Ser Arg Leu Glu Asp
1               5                   10

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Asp Thr Gln Lys His Arg Val Asp Phe Leu Gln
1               5                   10

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Thr Gln Lys His Arg Val Asp
1               5

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

His Arg Val Asp Phe Leu Gln
1               5

(2) INFORMATION FOR SEQ ID NO:21:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:21:

Asp Thr Gln Lys His
1               5

(2) INFORMATION FOR SEQ ID NO:22:

(i) SEQUENCE CHARACTERISTICS:
             (A) LENGTH: 4 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:22:

Thr Gln Lys His
1

(2) INFORMATION FOR SEQ ID NO:23:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:23:

Leu Glu Asp Thr Gln Lys
1               5

(2) INFORMATION FOR SEQ ID NO:24:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:24:

Leu Glu Asp Thr Gln
1               5

(2) INFORMATION FOR SEQ ID NO:25:

(i) SEQUENCE CHARACTERISTICS:
             (A) LENGTH: 4 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:25:

Leu Glu Asp Thr
1

(2) INFORMATION FOR SEQ ID NO:26:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "N-acetyl Leucine - Modified at residue #1 by
                addition of acetyl group at amine (HN-COCH3)"

(ix) FEATURE:
            (A) NAME/KEY: Modified-site
            (B) LOCATION: 7
            (D) OTHER INFORMATION: /product= "amide-substituted
                histidine"
                /note= "hydroxyl group of histidine -COOH group
                substituted with amide group."

(xi) SEQUENCE DESCRIPTION: SEQ ID NO:26:

Xaa Glu Asp Thr Gln Lys Xaa
1               5

(2) INFORMATION FOR SEQ ID NO:27:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "N-acetyl Leucine - Modified at residue #1 by
                substituting acetyl group at amine (HN-COCH3)"

(xi) SEQUENCE DESCRIPTION: SEQ ID NO:27:

Xaa Glu Asp Thr Gln Lys His
1               5

(2) INFORMATION FOR SEQ ID NO:28:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "N-acetyl Leucine"
                /note= "N-Acetyl Leucine - modified at residue #1 by
                substitution of acetyl group at amine (HN-COCH3)."

(xi) SEQUENCE DESCRIPTION: SEQ ID NO:28:

Leu Glu Asp Thr Gln Lys Xaa
1               5

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Leu Ile Pro Ile Ile Glu Gln Arg Arg Gln Lys Pro Gly Thr Asp Ala
1               5                   10                  15
Ile Ser (2) INFORMATION FOR SEQ ID NO:30:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Val Asp Lys Ile Ile Ala Asp Arg Lys Ala Ser Gly Glu Gln Ser Asp
1               5                   10                  15
Asp Leu Leu Thr
            20

(2) INFORMATION FOR SEQ ID NO:31:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Val Asn Arg Met Lys Lys Ser Arg Leu Asn Asp Lys Gln Lys His Arg
1               5                   10                  15
Leu Asp Phe Leu Gln
            20

(2) INFORMATION FOR SEQ ID NO:32:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Val Lys Arg Met Lys Glu Ser Arg Leu Glu Asp Thr Gln Lys His Arg
1               5                   10                  15
Val Asp Phe Leu Gln

```
            20

(2) INFORMATION FOR SEQ ID NO:33:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Leu Gln Lys Thr Val Gln Glu His Tyr Gln Asp Phe Asp Lys Asn Ser
1               5                   10                  15
Val Arg Asp Ile Thr Gly
            20

(2) INFORMATION FOR SEQ ID NO:34:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Ile Leu Glu Lys Val Lys Glu His Gln Glu Ser Met Asp Met Asn Asn
1               5                   10                  15
Pro Gln Asp Phe Ile Asp
            20

(2) INFORMATION FOR SEQ ID NO:35:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Asp Glu Leu Leu Thr Glu His Arg Met Thr Trp Asp Pro Ala Gln Pro
1               5                   10                  15
Pro Arg Asp Leu Thr Glu
            20

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Val Ser Glu Arg Val Lys Glu His His Gln Ser Leu Asp Pro Asn Cys
1               5                   10                  15
Pro Arg Asp Leu Thr Asp
            20
```

ANTI-PEPTIDE ANTIBODY AGAINST HUMAN CYTOCHROME P450 3A4

CROSS-REFERENCE TO RELATED APPLICATIONS

This application claims benefit to provisional application No. 60/043,230, filed Apr. 10, 1997, now abandoned.

FIELD OF THE INVENTION

The present invention relates to an anti-peptide antibody raised against a portion of human cytochrome P450 3A4. A particular anti-peptide antibody was raised against a 21-amino acid peptide corresponding to residues 253–273 of human cytochrome P450 3A4, which is both specific to CYP3A4 and effectively inhibits CYP3A4 activity.

BACKGROUND OF THE INVENTION

The use of in vitro metabolism of therapeutic agents to address the potential in vivo induction, inhibition, drug-drug interaction and individual variability issues is known (for a recent review, see Rodrigues, 1994, *Biochem. Pharmacol.* 48: 2147–2156). Central to these studies is the unambiguous identification of specific drug-metabolizing enzyme(s), particularly human cytochrome P450 isoform(s) responsible for the metabolism of drugs. This objective can be achieved by using selective cytochrome P450 inhibitors, antibodies, recombinant cytochrome P450s and correlation analysis (Rodrigues, 1994, *Biochem. Pharmacol.* 48: 2147–2156).

Polyclonal or monoclonal antibodies produced against purified cytochrome P450 or specific peptide sequences unique to individual cytochrome P450 isoforms have been used to study the regulation, structure and function of cytochrome P450s.

Leeder et al. (1996, *Mol. Pharmacol.* 49: 234–243) used epitope mapping studies to identify a minimum antibody binding sequence in CYP3A1 located in the K-helix of the protein.

Gelboin et al. (1995, *Biochemical Pharmacology* 50(11):1841–1850) disclose a monoclonal antibody which is inhibitory to human cytochrome P450 3A3/4/5.

Cribb et al. (1995, *Drug Metabolism and Disposition* 23(7): 671–675) disclose antipeptide antibodies against two overlapping synthetic peptides from human CYP2D6. Antipeptide antibodies against one of these synthetic peptides substantially inhibited recombinant human CYP2D6 activity.

Despite these advances, there remains a substantial need for specific and inhibitory antibodies to members of the human cytochrome P450 class of enzymes, especially to human CYP3A4. The present invention addresses and meets this need.

SUMMARY OF THE INVENTION

The present invention relates to antibodies against human CYP3A4 which are specific to human CYP3A4 in relation to other human P450 enzymes and which also substantially inhibit human CYP3A4 enzyme activity.

The present invention particularly relates to anti-peptide antibodies raised against a portion of the human CYP3A4 protein which are specific to human CYP3A4 in relation to other human P450 enzymes and which also substantially inhibit human CYP3A4 enzyme activity.

A preferred aspect of the present invention relates to anti-peptide antibodies raised against a 21 amino acid peptide corresponding to amino acid 253–273 of human CYP3A4, which is Val Lys Arg Met Lys Glu Ser Arg Leu Glu Asp Thr Gln Lys His Arg Val Asp Phe Leu Gln (SEQ ID NO:1).

Another embodiment of the present invention relates to antibodies raised against a peptide wherein a cysteine residue has been introduced at the amino terminus of SEQ ID NO:1, resulting in Cys Val Lys Arg Met Lys Glu Ser Arg Leu Glu Asp Thr Gln Lys His Arg Val Asp Phe Leu Gln (SEQ ID NO:2).

A preferred embodiment of the present invention relates to antibodies raised against the peptide of SEQ ID NO:2 which has been coupled to keyhole limpet haemocyanin.

Another embodiment of the present invention relates to antibodies raised against the inhibitory epitope which is contained within the 21 amino acid region of SEQ ID NO:1. A specific embodiment of this portion of the invention are antibodies raised against the inhibitory epitope within SEQ ID NO:1, which preferably is Arg Leu Glu Asp Thr Gln Lys His Arg (SEQ ID NO:3). It is also within the scope of this portion of the invention to raise antibodies against a peptide wherein a cysteine residue has been introduced at the amino terminus of SEQ ID NO:3, resulting in Cys Arg Leu Glu Asp Thr Gln Lys His Arg (SEQ ID NO:4) and to couple this peptide to keyhole limpet haemocyanin prior to immunization.

Another especially preferred embodiment of the present invention relates to antibodies raised against the inhibitory epitope contained within the 21 amino acid region of SEQ ID NO:1. This epitope comprises the middle portion of SEQ ID NO:1, preferably Leu Glu Asp Thr Gln Lys His (SEQ ID NO:9). As with all disclosed peptides within this specification, it is preferable to introduce a cysteine residue at the amino terminus (Cys Leu Glu Asp Thr Gln Lys His (SEQ ID NO:15) and to couple this peptide to keyhole limpet haemocyanin prior to immunization to generate anti-peptide antibodies of the present invention.

Another especially preferred embodiment of the present invention relates to antibodies raised against the inhibitory epitope contained within the 21 amino acid region of SEQ ID NO:1. This epitope comprises the middle portion of SEQ ID NO:1, preferably Glu Asp Thr Gln Lys His (SEQ ID NO:10). As with all disclosed peptides within this specification, it is preferable to introduce a cysteine residue at the amino terminus (Cys Glu Asp Thr Gln Lys His (SEQ ID NO: 16) and to couple this peptide to keyhole limpet haemocyanin prior to immunization to generate anti-peptide antibodies of the present invention.

An additional embodiment of the present invention relates to antibodies raised against peptides which comprise at least a portion of the peptide comprising the inhibitory epitope of SEQ ID NO:3. Such antibodies may be raised against peptides which include, but are not necessarily limited to, Val Lys Arg Met Lys Glu Ser Arg Leu Glu Asp Thr Gln Lys His Arg Val Asp (SEQ ID NO:5); Val Lys Arg Met Lys Glu Ser Arg Leu Glu Asp Thr Gln Lys His (SEQ ID NO:6); Leu Glu Asp Thr Gln Lys His Arg Val Asp (SEQ ID NO:7); and, Lys Glu Ser Arg Leu Glu Asp Thr Gln Lys His (SEQ ID NO:8). As disclosed above for antibodies raised against SEQ ID NOS: 1 and 2, it is preferable that the antibodies of this portion of the invention to raise antibodies against theses peptides wherein a cysteine residue has been introduced at the amino terminus (i.e., SEQ ID NOS: 11–14, respectively) of the synthetic peptide and this peptide has been coupled to keyhole limpet haemocyanin prior to immunization.

Especially preferred antibodies are anti-peptide antibodies raised against the synthetic peptide or protein fragments disclosed in SEQ ID NO:3, SEQ ID NO:9 and SEQ ID NO:10 and their respective cysteine-modified forms, disclosed as SEQ ID NOS:4, 15 and 16.

The anti-peptide antibodies of the present invention are specific to human CYP3A4 in relation to other human P450 enzymes and show an ability to inhibit at least about 80% of human CYP3A4 activity.

A preferred anti-peptide antibody of the present invention is specific to human CYP3A4 in relation to other human P450 enzymes and shows an ability to inhibit at least about 90% of human CYP3A4 activity.

An especially preferred anti-peptide antibody of the present invention is specific to human CYP3A4 in relation to other human P450 enzymes and shows an ability to inhibit at least about 90% to about 95% of human CYP3A4 activity.

The present invention relates to a synthetic peptide or protein fragment which is useful for generating antibodies against human CYP3A4 which are specific in relation to other human P450 enzymes and which also substantially inhibit human CYP3A4 enzyme activity.

A preferred embodiment of the present invention relates to a 21 amino acid synthetic peptide or protein fragment corresponding to amino acid 253–273 of human CYP3A4, which is Val Lys Arg Met Lys Glu Ser Arg Leu Glu Asp Thr Gln Lys His Arg Val Asp Phe Leu Gln (SEQ ID NO:1).

Another aspect of the present invention relates to a cysteine-modified version of SEQ ID NO:1, which is Cys Val Lys Arg Met Lys Glu Ser Arg Leu Glu Asp Thr Gln Lys His Arg Val Asp Phe Leu Gln (SEQ ID NO:2). Additionally, this portion of the invention relates to the peptide of SEQ ID NO:2 which has been coupled to keyhole limpet haemocyanin.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:1 is Arg Leu Glu Asp Thr Gln Lys His Arg (SEQ ID NO:3). It is also within the scope of this portion of the invention to introduce a cysteine residue at the amino terminus (Cys Arg Leu Glu Asp Thr Gln Lys His Arg (SEQ ID NO:4) and to couple this peptide to keyhole limpet haemocyanin prior to immunization.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:3 is Leu Glu Asp Thr Gln Lys His (SEQ ID NO:9). It is also within the scope of this portion of the invention to introduce a cysteine residue at the amino terminus (Cys Leu Glu Asp Thr Gln Lys His (SEQ ID NO:15) and to couple this peptide to keyhole limpet haemocyanin prior to immunization.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:10 is Glu Asp Thr Gln Lys His (SEQ ID NO:10). It is also within the scope of this portion of the invention to introduce a cysteine residue at the amino terminus (Cys Glu Asp Thr Gln Lys His (SEQ ID NO:16) and to couple this peptide to keyhole limpet haemocyanin prior to immunization.

The present invention also relates to synthetic peptides or protein fragments which comprise a biologically active portion of the inhibitory epitope contained within SEQ ID NO:1 and SEQ ID NO:3 including but not necessarily limited to Val Lys Arg Met Lys Glu Ser Arg Leu Glu Asp Thr Gln Lys His Arg Val Asp (SEQ ID NO:5); Val Lys Arg Met Lys Glu Ser Arg Leu Glu Asp Thr Gln Lys His (SEQ ID NO:6); Leu Glu Asp Thr Gln Lys His Arg Val Asp (SEQ ID NO:7); and, Lys Glu Ser Arg Leu Glu Asp Thr Gln Lys His (SEQ ID NO:8). As disclosed above for peptides of SEQ ID NOS: 1 and 2, it is preferable that these peptides have a cysteine residue at the amino terminus and the respective peptide (Cys Val Lys Arg Met Lys Glu Ser Arg Leu Glu Asp Thr Gln Lys His Arg Val Asp (SEQ ID NO:11); Cys Val Lys Arg Met Lys Glu Ser Arg Leu Glu Asp Thr Gln Lys His (SEQ ID NO:12); Cys Leu Glu Asp Thr Gln Lys His Arg Val Asp (SEQ ID NO:13); and, Cys Lys Glu Ser Arg Leu Glu Asp Thr Gln Lys His (SEQ ID NO:14). The peptides disclosed in SEQ ID NOS: 11–14 are then coupled to keyhole limpet haemocyanin prior to immunization.

An especially preferred synthetic peptide or protein fragment of the present invention are SEQ ID NO:3, SEQ ID NO:9 and SEQ ID NO:10 and their respective cysteine-modified forms, disclosed as SEQ ID NOS:4, 15 and 16.

BRIEF DESCRIPTION OF THE DRAWINGS

FIG. 2A and FIG. 2B show western blot detection of cytochrome P450 in microsomal samples. Microsomes (50 μg) prepared from human B-lymphoblastoid cells which expressed specific human cytochrome P450 as indicated were immunoblotted with antibody raised against the peptide disclosed in SEQ ID NO:1 to determine the specificity of antibody (Panel A). The levels of immunodetectable CYP3A4 in human liver microsomes (Panel B) with peptide antibody were determined and quantified as described in Example Section 1.

DETAILED DESCRIPTION OF THE INVENTION

Figure 1:
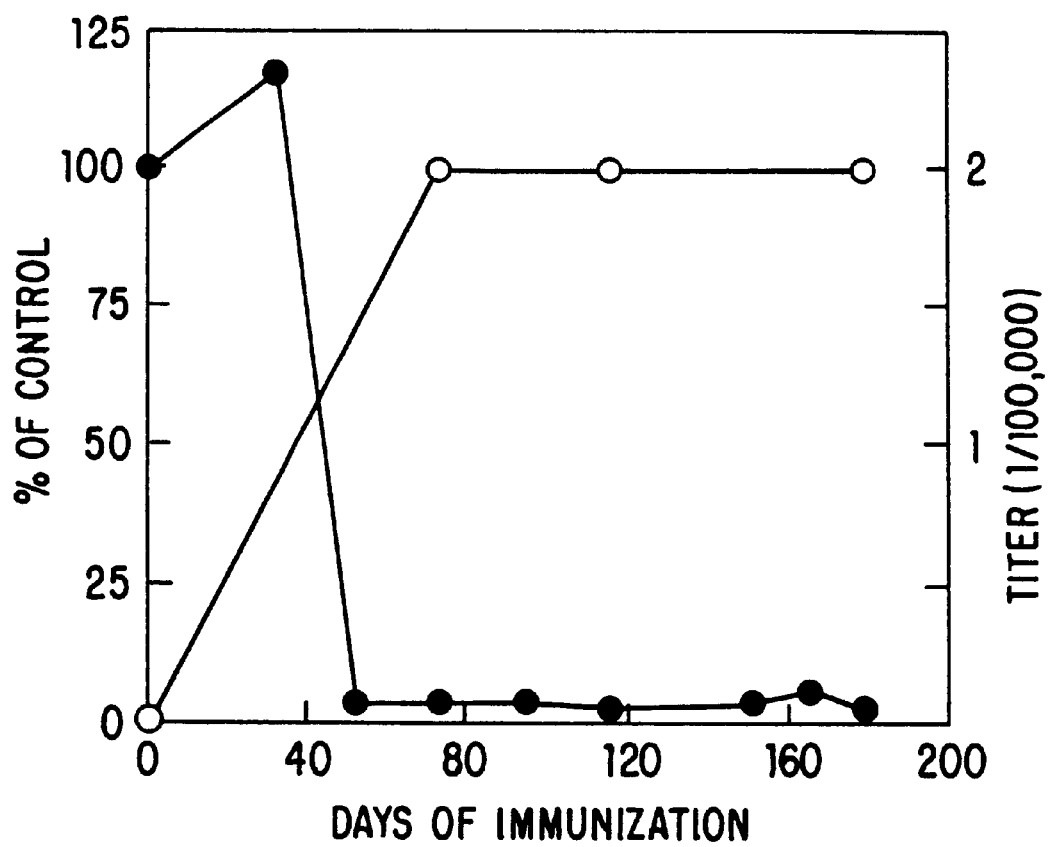
FIG. 1 shows the effect of anti-peptide antisera (raised against the peptide disclosed in SEQ ID NO:1) on testosterone 6β-hydroxylation. Human liver microsomes containing 0.13 nmol of cytochrome P450 were preincubated with 0.2 ml sera collected during the course of immunization. Testosterone 6β-hydroxylase activity (●) was measured as described in Example Section 1. The control activity (with preimmune serum) was 2.88 nmol/min/nmol P450. The titers (○) of the antisera were determined by ELISA.

The present invention relates to antibodies against human CYP3A4 which are specific to human CYP3A4 in relation to other human P450 enzymes and which also substantially inhibits human CYP3A4 enzyme activity.

The present invention particularly relates to anti-peptide antibodies raised against a portion of the human CYP3A4 protein which are specific to human CYP3A4 in relation to other human P450 enzymes and which also substantially inhibits human CYP3A4 enzyme activity.

The term "specific" or "specificity" as used herein regarding antibodies against human CYP3A4 mean that these antibodies do not cross-react with the major human cytochrome P450 isoforms in the 1A, 2A, 2C, 2D, 2E, 3A subfamilies.

As used herein, the term "CYP" corresponds to cytochrome P450.

As used herein, the term "ELISA" corresponds to enzyme-linked immunosorbent assay.

As used herein, "KLH" correspond to keyhole limpet haemocyanin.

As used herein, the term "THF" corresponds to tetrahydrofuran.

As used herein, the term "TFA" corresponds to trifluoroacetic acid.

As used herein, the term "LKM-1 autoantibodies" corresponds to liver-kidney microsomal-1 autoantibodies.

The term "substantially inhibit", "inhibit", etc. as used herein regarding antibodies against human CYP3A4 mean that these antibodies inhibit at least about 80–95% of human CYP3A4 activity in vitro.

The present invention particularly relates to anti-peptide antibodies raised against a portion of the human CYP3A4 protein which are specific in relation to other human P450 enzymes and which also substantially inhibit human CYP3A4 enzyme activity.

A preferred aspect of the present invention relates to anti-peptide antibodies raised against a 21 amino acid peptide corresponding to amino acid 253–273 of human CYP3A4, which is Val Lys Arg Met Lys Glu Ser Arg Leu Glu Asp Thr Gln Lys His Arg Val Asp Phe Leu Gln (SEQ ID NO:1). In regard to this aspect of the present invention, antibodies are raised a peptide wherein a cysteine residue has been introduced at the amino termimus of SEQ ID NO:1, resulting in Cys Val Lys Arg Met Lys Glu Ser Arg Leu Glu Asp Thr Gln Lys His Arg Val Asp Phe Leu Gln (SEQ ID NO:2). In an especially preferred aspect of this portion of the invention, the peptide as disclosed in SEQ ID NO:2 is coupled to keyhole limpet haemocyanin.

An especially preferred embodiment of the present invention relates to antibodies raised against the inhibitory epitope contained within the 21 amino acid region of SEQ ID NO:1. This epitope comprises the middle portion of SEQ ID NO:1, preferably Arg Leu Glu Asp Thr Gln Lys His Arg (SEQ ID NO:3). As with all disclosed peptides within this specification, it is preferable to introduce a cysteine residue at the amino terminus (Cys Arg Leu Glu Asp Thr Gln Lys His Arg (SEQ ID NO:4) and to couple this peptide to keyhole limpet haemocyanin prior to immunization to generate anti-peptide antibodies of the present invention.

Another especially preferred embodiment of the present invention relates to antibodies raised against the inhibitory epitope contained within the 21 amino acid region of SEQ ID NO:1. This epitope comprises the middle portion of SEQ ID NO:1, preferably Leu Glu Asp Thr Gln Lys His (SEQ ID NO:9). As with all disclosed peptides within this specification, it is preferable to introduce a cysteine residue at the amino terminus (Cys Leu Glu Asp Thr Gln Lys His (SEQ ID NO:15) and to couple this peptide to keyhole limpet haemocyanin prior to immunization to generate anti-peptide antibodies of the present invention.

Another especially preferred embodiment of the present invention relates to antibodies raised against the inhibitory epitope contained within the 21 amino acid region of SEQ ID NO:1. This epitope comprises the middle portion of SEQ ID NO:1, preferably Glu Asp Thr Gln Lys His (SEQ ID NO:10). As with all disclosed peptides within this specification, it is preferable to introduce a cysteine residue at the amino terminus (Cys Glu Asp Thr Gln Lys His (SEQ ID NO:16) and to couple this peptide to keyhole limpet haemocyanin prior to immunization to generate anti-peptide antibodies of the present invention.

Therefore, especially preferred antibodies are anti-peptide antibodies raised against the synthetic peptide or protein fragments disclosed in SEQ ID NO:3, SEQ ID NO:9 and SEQ ID NO:10 and their respective cysteine-modified forms, disclosed as SEQ ID NOS:4, 15 and 16.

Yet another embodiment of the present invention relates to antibodies raised against peptides which comprise at least a portion of the peptide comprising the inhibitory epitope of SEQ ID NO:3. Such antibodies may be raised against peptides which include, but are not necessarily limited to, Val Lys Arg Met Lys Glu Ser Arg Leu Glu Asp Thr Gln Lys His Arg Val Asp (SEQ ID NO:5); Val Lys Arg Met Lys Glu Ser Arg Leu Glu Asp Thr Gln Lys His (SEQ ID NO:6); Leu Glu Asp Thr Gln Lys His Arg Val Asp (SEQ ID NO:7); and, Lys Glu Ser Arg Leu Glu Asp Thr Gln Lys His (SEQ ID NO:8). As disclosed above for antibodies raised against SEQ ID NOS: 1 and 2, it is preferable that the antibodies of this portion of the invention to raise antibodies against theses peptides wherein a cysteine residue has been introduced at the amino terminus (i.e., SEQ ID NOS: 11–14, respectively) of the synthetic peptide and this peptide has been coupled to keyhole limpet haemocyanin prior to immunization. It will be within the purview of the skilled artisan to utilize alternative carriers to KLH, including but not limited to bovine serum albumin, ovalbumin, mouse serum albumin or rabbit serum albumin.

The present invention relates to a synthetic peptide or protein fragment which is useful for generating antibodies against human CYP3A4 which are specific in relation to other human P450 enzymes and which also substantially inhibit human CYP3A4 enzyme activity.

A preferred embodiment of the present invention relates to a 21 amino acid synthetic peptide or protein fragment corresponding to amino acid 253–273 of human CYP3A4, which is Val Lys Arg Met Lys Glu Ser Arg Leu Glu Asp Thr Gln Lys His Arg Val Asp Phe Leu Gln (SEQ ID NO:1).

Another aspect of the present invention relates to a cysteine-modified version of SEQ ID NO:1, which is Cys Val Lys Arg Met Lys Glu Ser Arg Leu Glu Asp Thr Gln Lys His Arg Val Asp Phe Leu Gln (SEQ ID NO:2). Additionally, this portion of the invention relates to the peptide of SEQ ID NO:2 which has been coupled to keyhole limpet haemocyanin.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:1 is Arg Leu Glu Asp Thr Gln Lys His Arg (SEQ ID NO:3). It is also within the scope of this portion of the invention to introduce a cysteine residue at the amino terminus (Cys Arg Leu Glu Asp Thr Gln Lys His Arg (SEQ ID NO:4) and to couple this peptide to keyhole limpet haemocyanin prior to immunization.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:3 is Leu Glu Asp Thr Gln Lys His (SEQ ID NO:9). It is also within the scope of this portion of the invention to introduce a cysteine residue at the amino terminus (Cys Leu Glu Asp Thr Gln Lys His (SEQ ID NO:15) and to couple this peptide to keyhole limpet haemocyanin prior to immunization.

Another embodiment of the present invention relates to a synthetic peptide or protein fragment comprising the inhibitory epitope contained within the 21 amino acid region of SEQ ID NO:1. A preferred peptide comprising the inhibitory epitope from SEQ ID NO:10 is Glu Asp Thr Gln Lys His (SEQ ID NO:10). It is also within the scope of this portion of the invention to introduce a cysteine residue at the amino terminus (Cys Glu Asp Thr Gln Lys His (SEQ ID NO:16) and to couple this peptide to keyhole limpet haemocyanin prior to immunization.

Therefore, especially preferred synthetic peptides or protein fragments of the present invention are SEQ ID NO:3, SEQ ID NO:9 and SEQ ID NO:10 and their respective cysteine-modified forms, disclosed as SEQ ID NOS:4, 15 and 16.

The present invention also relates to synthetic peptides or protein fragments which comprise a biologically active portion of the inhibitory epitope contained within SEQ ID NO:1 and SEQ ID NO:3 including but not necessarily limited to Val Lys Arg Met Lys Glu Ser Arg Leu Glu Asp Thr Gln Lys His Arg Val Asp (SEQ ID NO:5); Val Lys Arg Met Lys Glu Ser Arg Leu Glu Asp Thr Gln Lys His (SEQ ID NO:6); Leu Glu Asp Thr Gln Lys His Arg Val Asp (SEQ ID NO:7); and, Lys Glu Ser Arg Leu Glu Asp Thr Gln Lys His (SEQ ID NO:8). As disclosed above for peptides of SEQ ID NOS: 1 and 2, it is preferable that these peptides have a cysteine residue at the amino terminus and the respective peptide (Cys Val Lys Arg Met Lys Glu Ser Arg Leu Glu Asp Thr Gln Lys His Arg Val Asp (SEQ ID NO:11); Cys Val Lys Arg Met Lys Glu Ser Arg Leu Glu Asp Thr Gln Lys His (SEQ ID NO:12); Cys Leu Glu Asp Thr Gln Lys His Arg Val Asp (SEQ ID NO:13); and, Cys Lys Glu Ser Arg Leu Glu Asp Thr Gln Lys His (SEQ ID NO:14). The peptides disclosed in SEQ ID NOS: 11–14 are then coupled to keyhole limpet haemocyanin prior to immunization.

Specific and inhibitory antibodies are extremely useful tools for the identification of specific cytochrome P450 involvement in the in vitro metabolism of therapeutic agents. However, due to a limited supply of purified single cytochrome P450s used for immunization, antibodies against specific human cytochrome P450s are not always available for such studies. In addition, antibodies raised against specific cytochrome P450 isolated from human liver tissues potentially could cross-react with other cytochrome P450 isoforms (e.g., see Parkinson and Gemzik, 1991, In *Methods in Enzymology* 206: 233–245). The reason for nonspecificity is possibly due to contamination with structurally related cytochrome P450s which are difficult to separate. Cross-reactivity has also been reported even when purified recombinant cytochrome P450 was used as an immunogen (Belloc, et al., 1996, *Toxicology* 106: 207–219; Soucek, et al., 1995, *Biochemistry* 34: 16013–16021). This is because some of these antibodies can recognize regions of high sequence homology in related cytochrome P450s. The present invention overcomes this problem by using a peptide which targets a specific region of the protein as an immunogen so as to generate antibodies with less potential for cross-reactivity.

The present invention relates to synthetic peptides or protein fragments and the resulting anti-peptide antibodies which are specific and inhibitory against cytochrome P450s. Partially inhibitory antibodies are not useful for the identification of the specific cytochrome P450s responsible for the metabolism of therapeutic agents since one can not determine whether partial inhibition is due to the involvement of additional cytochrome P450 isoforms or to the weak inhibitory property of the antibodies. The anti-peptide antibodies of the present invention are specific to human CYP3A4 in relation to other human P450 enzymes and show an ability to inhibit at least about 80% of human CYP3A4 activity, preferably at least about 90% of human CYP3A4 activity, and especially preferable wherein the anti-peptide antibody inhibits at least about 90% to about 95% of human CYP3A4 activity.

To this end, the present invention especially relates to synthetic peptides or protein fragments and the resulting production of anti-peptide antibodies that are inhibitory against a 21-amino acid peptide corresponding to amino acid 253–273 of human CYP3A4. The polyclonal antibodies raised against this 21 amino acid synthetic peptide show greater than 90–95% inhibition on human CYP3A4-mediated reactions.

Many criteria must be considered in any attempt to select a peptide to produce inhibitory antibody with high specificity for a single isoform of cytochrome P450. These criteria include structural characteristics of the peptide, degree of sequence homology of the targeted peptide compared to the sequence of other isoforms, and the location of the regions in the enzyme involved in substrate binding and recognition. Because three-dimensional structures of mammalian cytochrome P450s are not available, the proposed substrate recognition sites have been located by using amino acid sequence alignment with bacterial cytochrome P450s (see Lewis, 1995, *Xenobiotica* 25: 333–366; Edwards et al., 1989, *Biochemistry* 28: 3762–3770; Gotoh, 1992, *J. Biol. Chem.* 267: 83–90).

The peptide of SEQ ID NO:1 is hydrophilic, with high surface probability and located in the loop region between G helix and H helix which is near to but not in any substrate recognition sites proposed previously. When rabbits were immunized with the same KLH-conjugated peptide comprising the 21 amino acid sequence of SEQ ID NO:1 (i.e., SEQ ID NO:2 conjugated to KLH), high titer antibodies against CYP3A4 were produced in all rabbits as judged by ELISA. However, antibodies produced by certain rabbits were not inhibitory. Thus, only those highly inhibitory antisera were purified and characterized. It will be within the purview of the artisan of ordinary skill to test antisera from each animal to verify generation of inhibitory antibodies raised against the synthetic peptides of the present invention. It can be expected that approximately between 10% to about 30% of animals will test positive for inhibitory antisera.

On the basis of the results from western blots and inhibition studies, the anti-peptide antibody against SEQ ID NO:1 can bind to both native and denatured forms of human CYP3A4. The binding of this antibody to CYP3A4, but not other cytochrome P450 isoforms, shows that the amino acid sequence in this loop region is unique for CYP3A4.

Production of inhibitory antibodies against CYP3A4 peptide provides a valuable tool for evaluating the role of human CYP3A4 in mediating in vitro metabolism of therapeutic agents. In addition, noninhibitory antibodies can be used for cytochrome P450 epitope investigation, gene expression and regulation, tissue localization, affinity purification for CYP3A4 and many other studies.

Monospecific antibodies to the synthetic peptides set forth in this disclosure, including but not limited to the synthetic peptides set forth in SEQ ID NOS:1 and 2; SEQ ID NOS:3 and 4; SEQ ID NOS:9 and 15; and SEQ ID NOS:10 and 16 are purified from mammalian antisera containing antibodies reactive against the respective peptide or are prepared as monoclonal antibodies reactive with the respective peptide using the technique of Kohler and Milstein (1975, *Nature* 256: 495–497) as described in detail in Harlow and Lane, 1988, In "Antibodies, a Laboratory Manual", Cold Spring Harbor Laboratory. Monospecific antibody as used herein is defined as a single antibody species or multiple antibody species with homogenous binding characteristics for the respective peptide. Homogenous binding as used herein refers to the ability of the antibody species to bind to a specific antigen or inhibitory epitope, such as those associated with and herein described within this disclosure from polyclonal sera for the respective synthetic peptide. These monoclonal specific antibodies are raised by immunizing animals such as mice, rats, guinea pigs, rabbits, goats, horses and the like, with an appropriate concentration of the respective peptide either with or without an immune adjuvant. It will also be within the purview of the skilled artisan to again, as described for raising polyclonal antibodies, utilize alternative carriers to KLH, including but not limited to bovine serum albumin, ovalbumin, mouse serum albumin or rabbit serum albumin.

Preimmune serum is collected prior to the first immunization. Each animal receives between about 0.1 mg and about 1000 mg of synthetic peptide associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the synthetic peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of synthetic peptide in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about –20° C.

Monoclonal antibodies (mAb) reactive with the respective peptide are prepared by immunizing inbred mice, preferably Balb/c, with the chosen synthetic peptide. The mice are immunized by the IP or SC route with about 1 mg to about 100 mg, preferably about 10 mg, of the synthetic peptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of the chosen synthetic peptide in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4–1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using the synthetic peptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-peptide mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques.

EXAMPLE 1

Specificity and Inhibitory Activity of Antibodies Raised Against Synthetic Peptides Corresponding to SEQ ID NOS:1 and 2

Materials.—Testosterone, 6b-hydroxytestosterone, phenacetin, tolbutamide, chlorzoxazone, corticosterone, glucose 6-phosphate, NADP, and glucose 6-phosphate dehydrogenase were purchased from Sigma (St. Louis, Mo.). Acetaminophen was obtained from Aldrich Chemical Co. (Milwaukee, Wis.). Methylhydroxytolbutamide and 6-hydroxychlorzoxazone were obtained from Research Biochemical International (Natick, Mass.). Bufuralol and 1'-hydroxy-bufuralol were purchased from Gentest Corp. (Woburn, Mass.). Microsomes prepared from human B-lymphoblastid cells expressing specific human cytochrome P450 isoforms, or from baculovirus infected cells expressing CYP3A4 or CYP3A5 were obtained from Gentest Corp (Woburn, Mass.). Midazolam was supplied by Hoffman-Laroche, Inc. (Nutley, N.J.). All other reagents and solvents were of high analytical grade supplied by Fisher Scientific (Fair Lawn, N.J.).

Human liver microsomal preparations were kindly provided by Dr. Judy Raucy (Agouron Institute, La Jolla, Calif.). Microsomes were prepared as described by Raucy and Lasker (1991, Isolation of P450 enzymes from human liver. In "Methods in Enzymology" (Waterman and Johnson, eds) Academic Press, San Diego, 206: 557–587). The pyrophosphate-washed microsomes were resuspended at a protein concentration of 10–15 mg/ml in 10 mM potassium phosphate buffer, pH 7.4 containing 0.25 M sucrose, and frozen at −80° C. until used. Protein concentrations and P450 contents were determined using the bicinchoninic acid procedure (Smith, et al., 1985, *Anal. Biochem.* 150: 76–85) and according to Omura and Sato (1964, *J. Biol. Chem.* 239: 2370–2378), respectively. Microsomes from cells containing human cytochrome P450 were obtained from Gentest Corp. (Woburn, Mass.).

Peptide Synthesis and Conjugation to Carrier Protein.— The peptide Val Lys Arg Met Lys Glu Ser Arg Leu Glu Asp Thr Gln Lys His Arg Val Asp Phe Leu Gln (SEQ ID NO:1) was synthesized on an Applied Biosystems 430 A peptide synthesizer using solid phase chemistry by AnaSpec Inc. (San Jose, Calif.). A cysteine residue was introduced to the N-terminus for use in conjugation to the carrier protein, resulting in Cys Val Lys Arg Met Lys Glu Ser Arg Leu Glu Asp Thr Gln Lys His Arg Val Asp Phe Leu Gln (SEQ ID NO:2). The peptide represented as SEQ ID NO:2 was coupled to keyhole limpet haemocyanin (KLH) using N-succinimidyl bromoacetate as a crosslinking reagent as described by Bernatowicz and Matsuedon (1986, Anal. Biochem. 155: 95–102).

Antibody Production and Purification.—The immunization was performed at HRP, Inc. (Denver, Pa.) according to the method of Vaitukaitis et al. (1971, *J. Clin. Endocr.* 33: 988–991). All animal protocols in this study were conducted in accordance with Merck Institutional Animal Care and Use Committee Guidelines. Rabbits were initially immunized with 100 μg of the peptide conjugated to KLH in complete Freund's adjuvant by intranodal injection and then by subcutaneous injection with 250 μg in Freund's incomplete adjuvant on day 20. Rabbits were continuously boosted at three-week intervals with 125 μg of antigen in Freund's incomplete adjuvant. Sera were collected ten days after each injection. IgG fractions were purified from rabbit sera by caprylic acid precipitation and ammonium sulfate fractionation (McKinney and Parkinson, 1987, *J. Immunological Methods* 96: 271–278.). The titers of the antisera were determined by ELISA as described (Harlow and Lane, 1988, In "Antibodies, a Laboratory Manual", Cold Spring Harbor Laboratory, pp. 555–612).

Western Blots—Human liver microsomes (15 μg) or microsomes from cells containing recombinant human cytochrome P450 (50 μg) were subjected to 10% SDS-polyacrylamide gel electrophoresis according to Laemmli (1970, *Nature* 227: 680–685) and transferred to a nitrocellulose membrane (Bio-Rad Laboratories, Hercules, Calif.) using the method of Towbin et al. (1979, *Proc. Natl. Acad. Sci. USA* 76: 4350–4354). The nitrocellulose sheets were blocked with nonfat dry milk, incubated with antibody and then treated with $^{125}$I-Protein A (Amersham Corp.). The immunoblotting intensity was quantified by the pdi Imaging Densitometer and Quantity One Software (pdi Inc., Huntington Station, N.Y.).

Immunoinhibition—Immunoinhibition was conducted by preincubating microsomes for 30 minutes at room temperature with various amounts of rabbit preimmune IgG or anti-peptide IgG. Reaction was started by addition of buffer, NADPH-generating system and substrate as described for the following enzyme assays.

Enzyme Assays—Testosterone 6β-hydroxylation was determined as described (Newton et al., 1995, *Drug Metab. Dispos.* 23: 154–158). Briefly, microsomal samples were incubated with 100 μM testosterone in 100 mM potassium phosphate buffer (pH 7.4) with 1 mM EDTA, 6 mM MgCl$_2$ and an NADPH-generating system consisting of 10 mM glucose 6-phosphate, 1 mM NADP and 0.35 units glucose 6-phosphate dehydrogenase in a total volume of 0.5 ml. Reactions were performed at 37° C. for 10 min with 0.34 mg of human liver microsomes containing 0.1 nmol cytochrome P450, and at 37° C. for 20 min with 0.25 mg of microsomes prepared from human B-lymphoblast cells. After reactions were stopped by adding 5 ml of CH$_2$Cl$_2$, the samples were spiked with 20 μl of 1 mM corticosterone as internal standard, vortexed and centrifuged at 3,000×g for 10 min.

The organic layer was removed and evaporated to dryness under nitrogen stream. Samples were dissolved in 0.2 ml of methanol and analyzed by HPLC. Phenacetin O-deethylation (Tassaneeyakul et al. 1993, *J. Pharmacol. Exp. Ther.* 265: 401–407.), tolbutamide methylhydroxylation (Knodell, et al., 1987, *J. Pharmacol. Exp. Ther.* 241: 1112–1119), bufuralol 1'-hydroxylation (Kronbach, 1991, In *Methods in Enzymology*, 206: 509–517), and chlorzoxazone 6-hydroxylation (Peter, et al., 1990, *Chem. Res. Toxicol.* 3: 566–573) were determined for CYP1A2, CYP2C9/10, CYP2D6, and CYP2E1-mediated reactions, respectively. The substrate concentrations and incubation time used for each assay were 100 $\mu$M phenacetin for 20 min, 200 $\mu$M tolbutamide for 60 min, 100 $\mu$M bufuralol for 10 min or 500 $\mu$M chlorzoxazone for 20 min. Reactions were quenched by adding 0.05 ml of 85% $H_3PO_4$. Samples were centrifuged at 14,000×g for 10 minutes, and the supernatants were directly injected for HPLC analysis.

Midazolam 1'-hydroxylation (Gorski et al., 1994, Biochem. Pharmacol. 47: 1643–1653) was assayed for CYP3A4 and CYP3A5. In this assay, 25 $\mu$M midazolam was incubated for 10 minutes with microsomes prepared from baculovirus infected cells, expressing either CYP3A4 or CYP3A5. The reactions were quenched by adding an equal volume of methanol.

HPLC Analysis—The HPLC used was a Shimadzu SCL 10A system controller consisting of two LC 10AS pumps, a SIL 10A automatic sample injector, SPD10A UV-VIS spectrophotometric detector and RF10A spectrofluoremetric detector. Aliquots of 50 $\mu$l samples from the testosterone 6$\beta$-hydroxylation incubation were injected onto a Zorbax ODS C18 column (4.6 mm×250 mm, 5 $\mu$, Sigma-Aldrich, Milwaukee, Wis.). Substrate and metabolite were eluted from the column with methanol (7.5% THF): $H_2O$(7.5% THF) by a linear gradient from 35% to 60% in 35 min at a flow rate of 1 ml/min and monitored at 254 nm. The retention times for 6$\beta$-hydroxy-testosterone, corticosterone and testosterone were 8.9, 17.5, and 25.2 min, respectively. Chromatographic analyses were carried out for phenacetin O-deethylation, tolbutamide methylhydroxylation, bufuralol 1'-hydroxylation and chlorzoxazone 6-hydroxylation on a Zorbax SB C8 column (4.6 mm×75 mm, 3.5$\mu$) at a flow rate of 2 ml/min by a linear gradient elution with the mobile phase which consisted of buffer A (10 mM of ammonium acetate and 0.1% TFA in $H_2O$) and buffer B (10 mM ammonium acetate and 0.1% TFA in 90% acetonitrile and 10% methanol). The percent of buffer B in the gradient, run time, detection wavelength and the retention times of substrate and its metabolite in these cytochrome P450-mediated reactions are as follows: phenacetin O-deethylation (5–40%, 12 min, 254 nm, acetaminophen 2.5 min and phenacetin 8.2 min); tolbutamide methylhydroxylation (10–65%, 10 min, 230 nm, 3-methyltolbutamide 5.3 min, and tolbutamide 7.9 min); bufuralol 1'-hydroxylation (15–45%, 10 min, excitation 252 nm and emission 302 nm by spectrofluorometer, 1'-hydroxybufuralol 3.8 min, and bufuralol 8.1 min); and chlorzoxazone 6-hydroxylation ( 8–65%, 10 min, 287 nm, 6-hydroxychlorxazone 4.1 min, and chlorzoxazone 6.4 min).

For midazolam 1'-hydroxylation, HPLC analysis was carried out on a Zorbax SB C8 column (4.6 mm×75 mm×3.5$\mu$) at a flow rate of 2 ml/min by a linear gradient elution (25 to 65% buffer B (10 $\mu$M ammonium acetate in 90% acetonitrile and 10% methanol) in 7 minutes, monitored at 254 nm) with the mobile phase which consisted of buffer A (10 $\mu$M ammonium acetate) and buffer B. The retention time is 5 minutes for midazolam 1'-hydroxylation and 6.5 minutes for midazolam.

Selection of Peptide—Table 1 shows the sequence alignment of major human cytochrome P450s in the loop region between helices G and H of CYP101 and CYP102 as proposed by Lewis (1995, *Xenobiotica* 25: 333–366). The peptide disclosed as SEQ ID NO:1 and corresponding to amino acid 253–273 of human CYP3A4 was selected based on low sequence homology among the major human cytochrome P450s, high surface probability, and hydrophilicity. The hydrophilicity was calculated according to the algorithm of Hopp and Woods (1981, *Proc. Natl. Acad Sci. USA* 78: 3824–3828) by averaging over a window of 7 residues. The surface probability was calculated according to a formula of Emini et al., 1985, *J. Virol.* 55: 836–839.

Production of Antibody—FIG. 1 shows that high titer antibody (1:204,800) was produced in immunized rabbit as judged by ELISA. Antiserum collected from rabbit strongly inhibited testosterone 6$\beta$-hydroxylation by human liver microsomes as well as recombinant CYP3A4. The production of inhibitory antibodies by rabbit is still maintained with repeated immunizations at three-week intervals. The IgG from rabbit was purified and characterized for its specificity in immunoblotting and immunoinhibition.

Specificity of Antibody—FIG. 2A shows that when a panel of microsomes prepared from human B-lymphoblastoid cells that expressed specific human cytochrome P450 isoforms were used for western blot analysis, only cytochrome P450 in microsomes containing human CYP3A4 was recognized by this anti-peptide antibody. No immunodetactable bands were observed in other microsomes containing CYP1A1, CYP1A2, CYP2A6, CYP2B6, CYP2C9, CYP2D6, CYP2E1 and CYP2F1.

FIG. 2B shows that this peptide antibody recognized a single protein band in human liver microsomes that comigrated with recombinant human CYP3A4. In liver microsome UC9402, no immunoreactive band was detected, consistent with the observation that this particular microsomal preparation had very little detectable testosterone 6$\beta$-hydroxylase activity.

Figure 3:
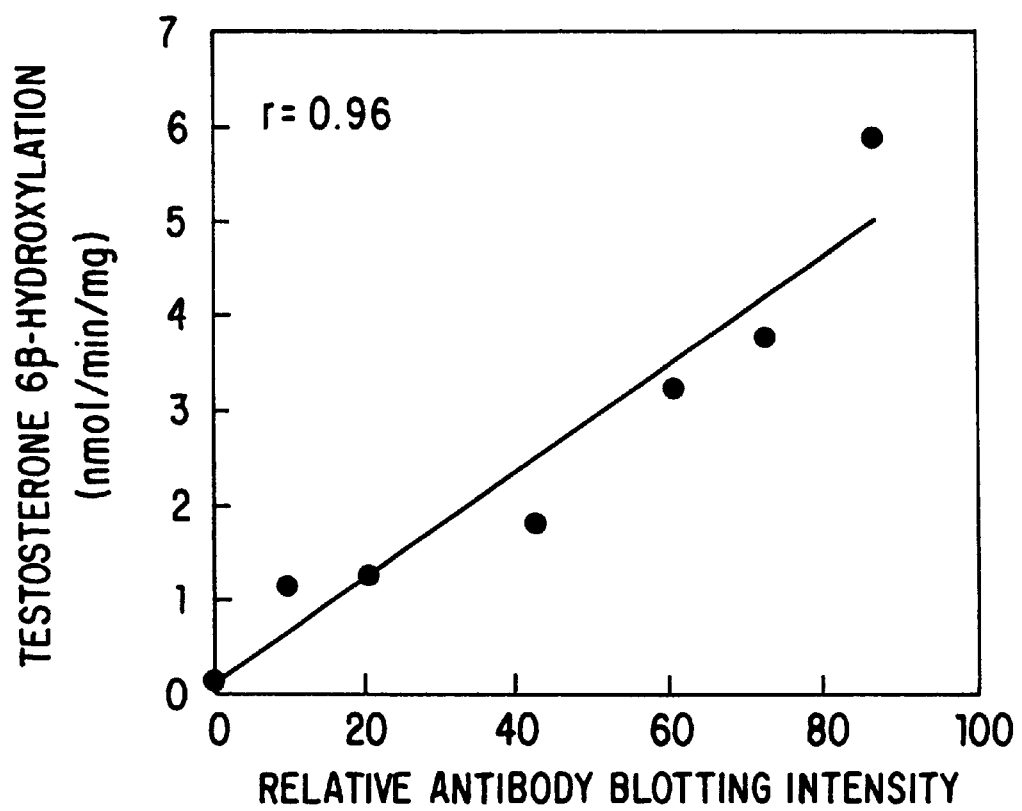
FIG. 3 shows the correlation of human CYP3A4 immunoblotting intensity with testosterone 6β-hydroxylation. Human CYP3A4-catalyzed testosterone 6β-hydroxylase activity was determined in seven human liver microsomes. The relative blotting intensity of CYP3A4 in human liver microsomes with antibody raised against the peptide disclosed in SEQ ID NO:1 was measured as shown in FIG. 2. The coefficients of correlation between testosterone 6β-hydroxylation and the blotting intensity were determined by linear regression analysis.

FIG. 3 shows that the quantity of immunoblotted protein in human liver microsomes correlated significantly with testosterone 6$\beta$-hydroxylase activity.

Figure 4A:
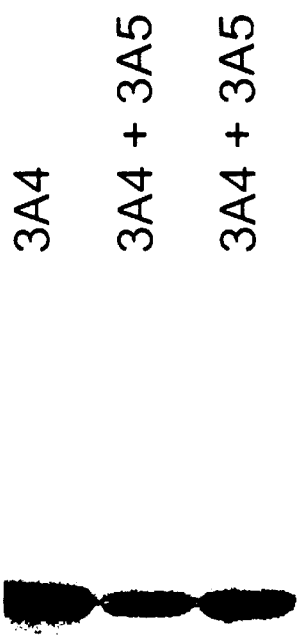
FIG. 4A and FIG. 4B show specificity of antibody raised against the peptide disclosed in SEQ ID NO:1. Western blot analysis of immunoblotted protein in microsomes prepared from baculovirus infected insect cells which expressed either CYP3A4 or CYP3A5 was performed as described in Example Section 1. Panel A shows western blot analysis of antibody raised against the peptide disclosed in SEQ ID NO:1. Panel B shows western blot analysis of antibody prepared against purified CYP3A4.
Figure 4B:
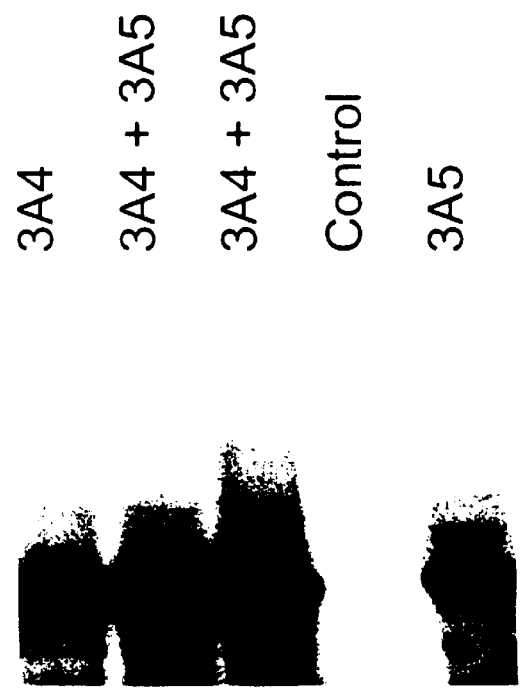

The specificity of this anti-peptide antibody was also evaluated against CYP3A5, a closely related isoform found in human liver. CYP3A5 differs from CYP3A4 by only five amino acids throughout this 21 amino acid region. FIG. 4A shows that the antibody raised against the peptide of SEQ ID NO:1 did not recognize CYP3A5. However, FIG. 4B shows that antibody prepared against purified CYP3A4 recognized both CYP3A4 and CYP3A5. Therefore, the antibody raised against the peptide comprising SEQ ID NOS:1 and 2 is extremely specific for CYP3A4. Consistent with this observed specificity, CYP3A5-catalyzed testosterone 6$\beta$-hydroxylation was not inhibited by this antibody.

Figure 5A:
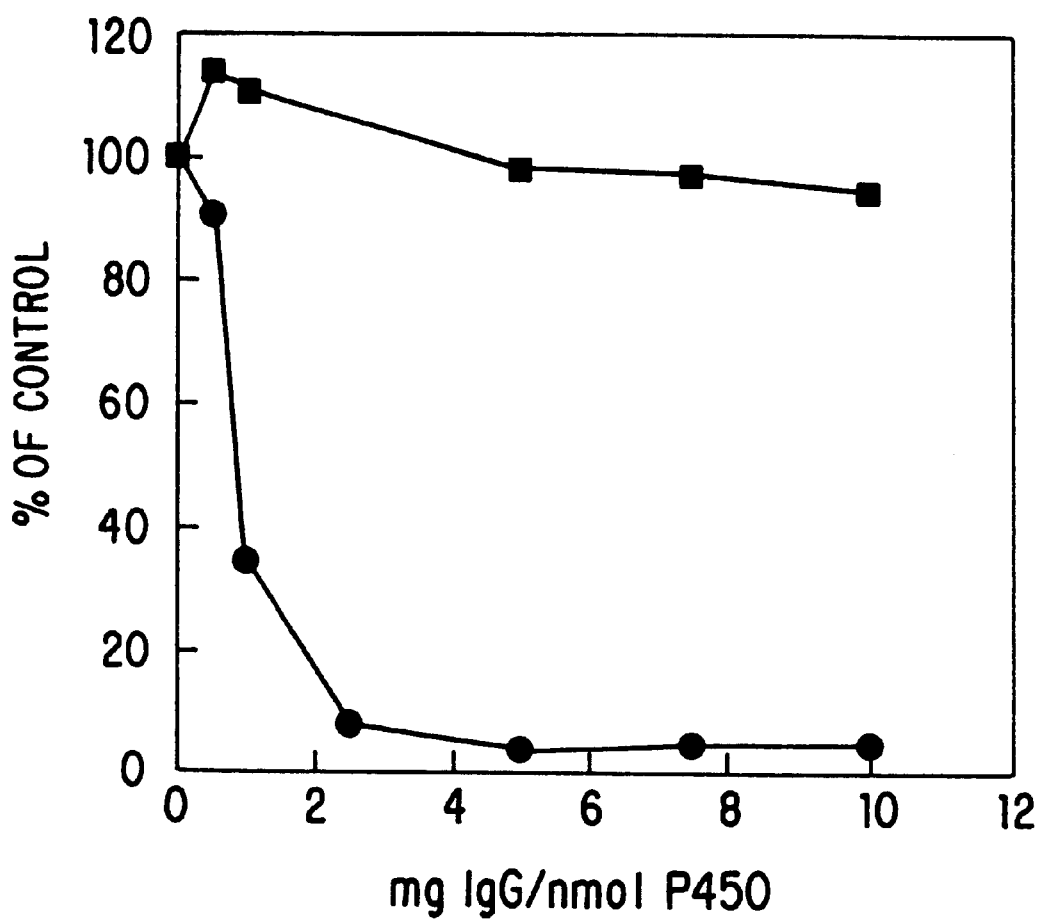
FIG. 5A and FIG. 5B show inhibition of testosterone 6β-hydroxylation by anti-peptide IgG. Human liver microsomes containing 0.1 nmol cytochrome P450 (Panel A) or microsomes (0.25 mg) prepared from human B-lymphoblastoid cells expressing human CYP3A4 and P450 reductase (Panel B) were preincubated with 0.5–10 mg of preimmune IgG (■) or anti-peptide IgG ([●] raised against the peptide disclosed in SEQ ID NO: 1). The control activities of testosterone 6β-hydroxylation were 3.15 nmol/min/nmol P450 for human liver microsome and 1.08 nmol/min/mg protein for microsome from cells expressing human CYP3A4 and P450 reductase.
Figure 5B:
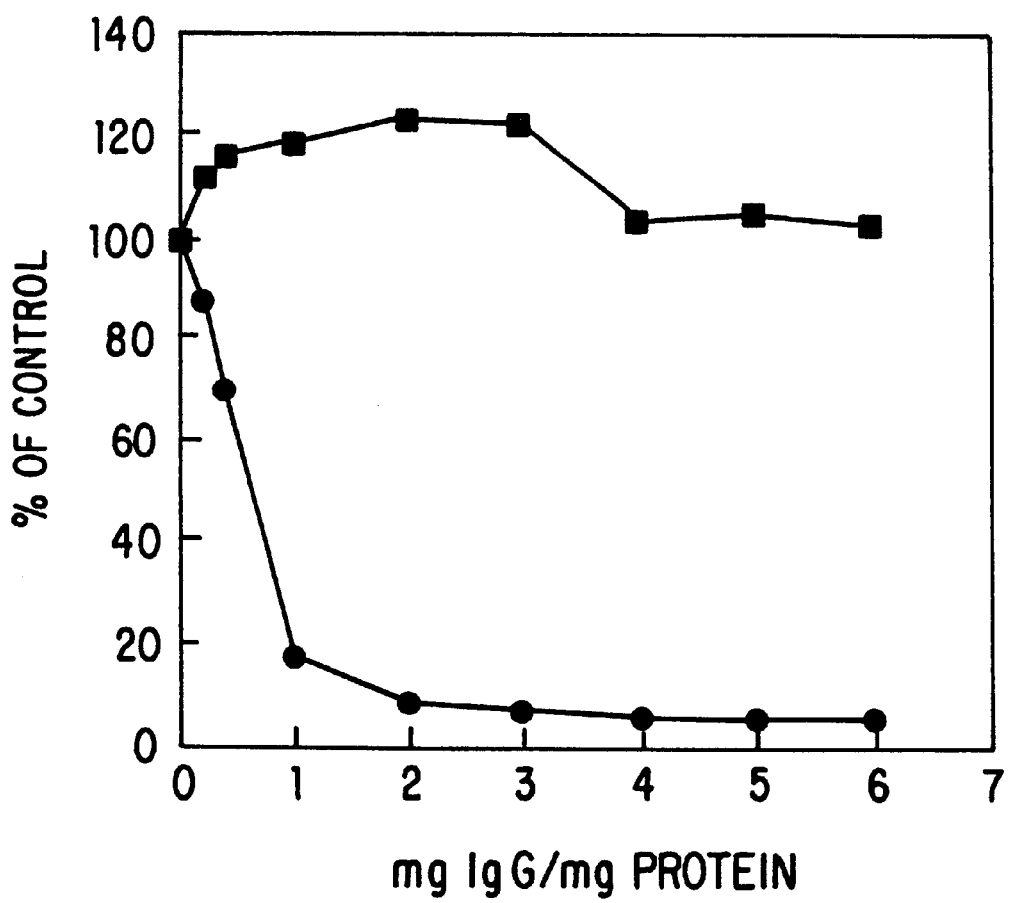
Figure 6:
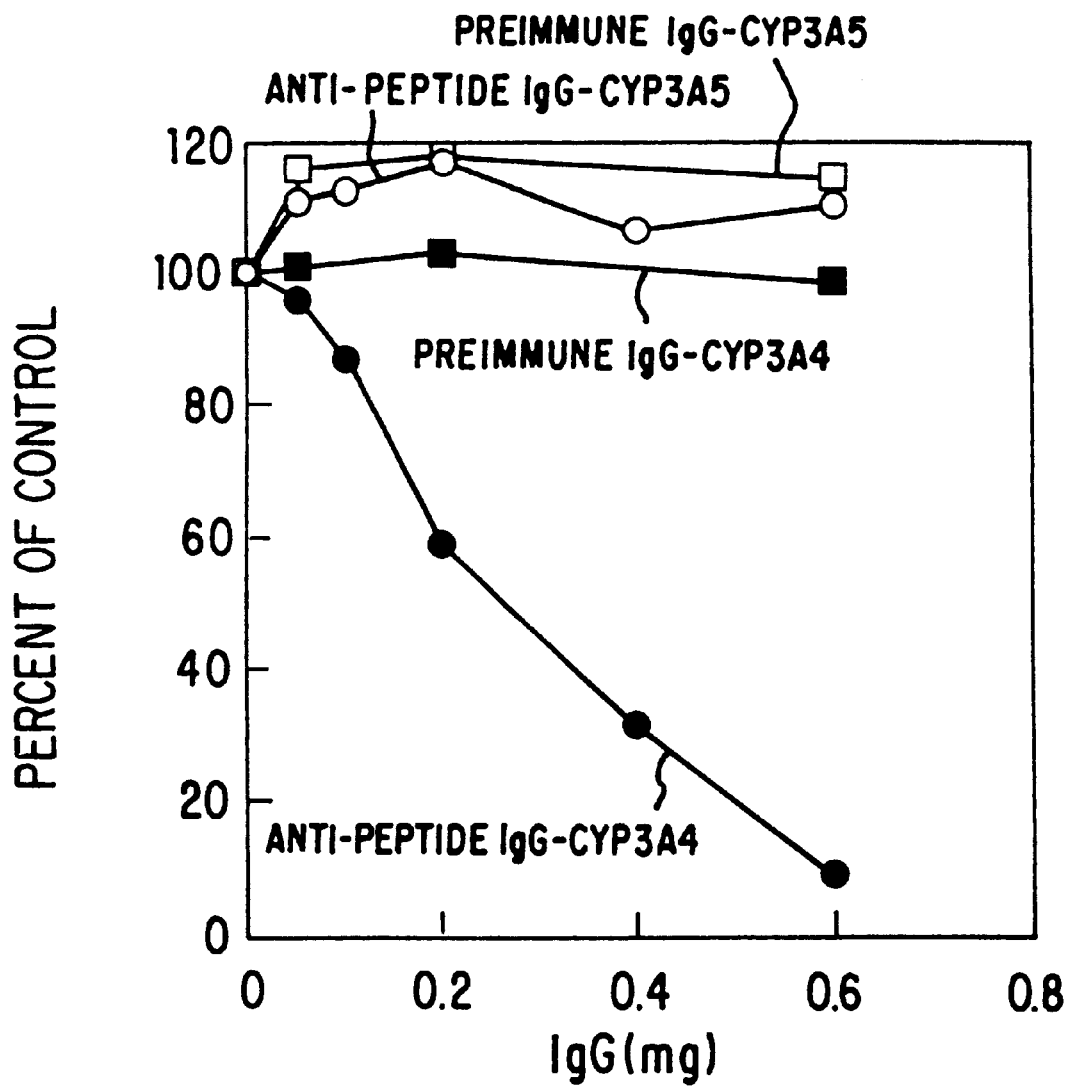
FIG. 6 shows the ability of antibody raised against the peptide disclosed in SEQ ID NO:1 to specifically and completely inhibit CYP3A4 activity associated with midazolam metabolism. CYP3A5-dependent midazolam metabolism is not affected. Microsomes prepared from baculovirus infected insect cells expressing either CYP3A4 (40 pmol) or CYP3A5 were preincubated with 0.05–0.6 mg of preimmune IgG or anti-peptide IgG raised against the peptide set forth in SEQ ID NO:1. The control activities of midazolam 1'-hydroxylation were 2.28 nmol/min/nmol 3A4 and 7.40 nmol/min/nmol 3A5.
Figure 7:
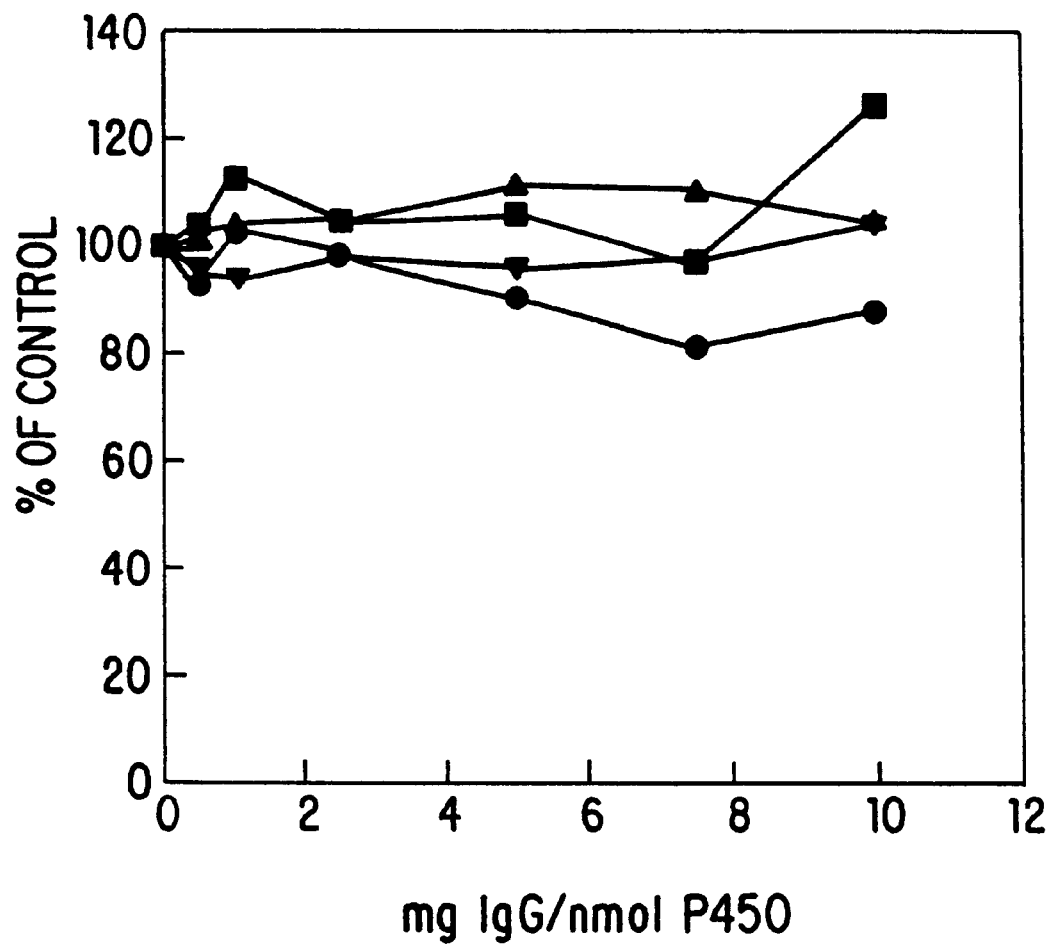
FIG. 7 shows the effect of antibody raised against the peptide disclosed in SEQ ID NO:1 on other CYP-mediated reactions. CYP1A2, CYP2C9/10, CYP2D6 and CYP2E1-mediated reactions were determined after 30 min preincubation of human liver microsomes containing 0.1 nmol cytochrome P450 with 0.5–10 mg of preimmune IgG or antipeptide IgG. The control activities were 2.39, 0.19, 3.46, and 7.35 nmol/min/nmol P450 for phenacetin O-deethylation (●), tolbutamide methylhydroxylation (■), bufuralol 1'-hydroxylation (Δ), and chlorzoxazone 6-hydroxylation (▼), respectively. There were no significant inhibitions on all reactions when preimmune serum was used in the incubations.

Effect of the Anti-peptide Antibody against CYP-Mediated Reactions—Purified IgG strongly inhibited testosterone 6$\beta$-hydroxylation, a CYP3A4-catalyzed reaction, in human liver microsomes (FIG. 5A) and microsome prepared from human B-lymphoblast cells expressing recombinant human CYP3A4 and P450 reductase (FIG. 5B). Greater than 90% of the activities were inhibited at an IgG to cytochrome P450 ratio of 2.5 in human liver microsomes. In addition, this purified anti-peptide IgG significantly inhibited midazolam metabolism (FIG. 6). Midazolam is a benzodiazapene compound used as an anesthetic and both CYP3A4 and CYP3A5 are known to be involved in midazolam metabolism. The data presented in FIG. 6 shows the specificity of this antibody to inhibit CYP3A4 while showing no ability to inhibit activity of the closely related human CYP3A5 protein activity in midazolam metabolism. In contrast, the purified IgG showed little or no inhibition toward other human cytochrome P450-mediated reactions, namely, phenacetin O deethylation, tolbutamide methylhydroxylation, bufuralol 1'-hydroxylation, and chlorzoxazone 6-hydroxylation (FIG. 7).

TABLE 1

Sequence Alignment Between CYP101, CYP102 and Some Major Human Cytochrome P450s[a]

| Isoform | Sequences | Res. # |
|---|---|---|
| predicted structure | ----G---> <- H | |
| CYP101 | LIPIIEQRRQKPGT----DAIS(SEQ ID NO:29) | 205–222 |
| CYP102 | VDKIIADRKASGEQSD--DLLT(SEQ ID NO:30) | 217–236 |
| CPY3A5 | VNRMKKSRLNDKQKHRL-DFLQ(SEQ ID NO:31) | 253–273 |
| CYP3A4 | VKRMKESRLEDTQKHRV-DFLQ(SEQ ID NO:32) | 253–273 |
| CYP1A2 | LQKTVQEHYQDFDKNSVRDITG(SEQ ID NO:33) | 264–285 |
| CYP2C9 | ILEKVKEHQESMDMNNPQDFID(SEQ ID NO:34) | 244–265 |
| CYP2D6 | DELLTEHRMTWDPAQPPRDLTE(SEQ ID NO:35) | 252–273 |
| CYP2E1 | VSERVKEHHQSLDPNCPRDLTD(SEQ ID NO:36) | 246–267 |

[a]Sequence alignment of human cytochrome P450s near the loop region between helices G and H of CYP101 and CYP102 as proposed by Lewis (1995, Xenobiotica 25: 333–366).

EXAMPLE 2
Specificity and Inhibitory Activity of Antibodies Raised Against Synthetic Peptides Comprising the Inhibitory Epitope of SEQ ID NOS:1 AND 2

Materials (including human liver microsome preparations) and methods in Example 2 were as described in Example 1.

Additional synthetic peptides comprising a portion of the coding sequence of SEQ ID NO:1 were generated in order to test the ability of each peptide to block the effect of inhibitory antibody raised against the peptide comprising SEQ ID NO:1 and 2. These peptides are as follows:

1. Val Lys Arg Met Lys Glu Ser Arg Leu Glu Asp Thr Gln Lys His Arg Val Asp (SEQ ID NO:5)
2. Val Lys Arg Met Lys Glu Ser Arg Leu Glu Asp Thr Gln Lys His (SEQ ID NO:6)
3. Val Lys Arg Met Lys Glu Ser Arg Leu Glu Asp (SEQ ID NO:17)
4. Asp Thr Gln Lys His Arg Val Asp Phe Leu Gln (SEQ ID NO:18)
5. Leu Glu Asp Thr Gln Lys His Arg Val Asp (SEQ ID NO:7)
6. Thr Gln Lys His Arg Val Asp (SEQ ID NO:19)
7. Lys Glu Ser Arg Leu Glu Asp Thr Gln Lys His (SEQ ID NO:8)
8. His Arg Val Asp Phe Leu Gln (SEQ ID NO:20)
9. Leu Glu Asp Thr Gln Lys His (SEQ ID NO:9)
10. Glu Asp Thr Gln Lys His (SEQ ID NO:10)
11. Asp Thr Gln Lys His (SEQ ID NO:21)
12. Thr Gln Lys His (SEQ ID NO:22)
13. Leu Glu Asp Thr Gln Lys (SEQ ID NO:23)
14. Leu Glu Asp Thr Gln (SEQ ID NO:24)
15. Leu Glu Asp Thr (SEQ ID NO:25)
16. (N-acetyl)-Leu Glu Asp Thr Gln Lys His-amide (SEQ ID NO:26)
17. (N-acetyl)-Leu Glu Asp Thr Gln Lys His (SEQ ID NO:27)
18. Leu Glu Asp Thr Gln Lys His-amide (SEQ ID NO:28).

Figure 8:
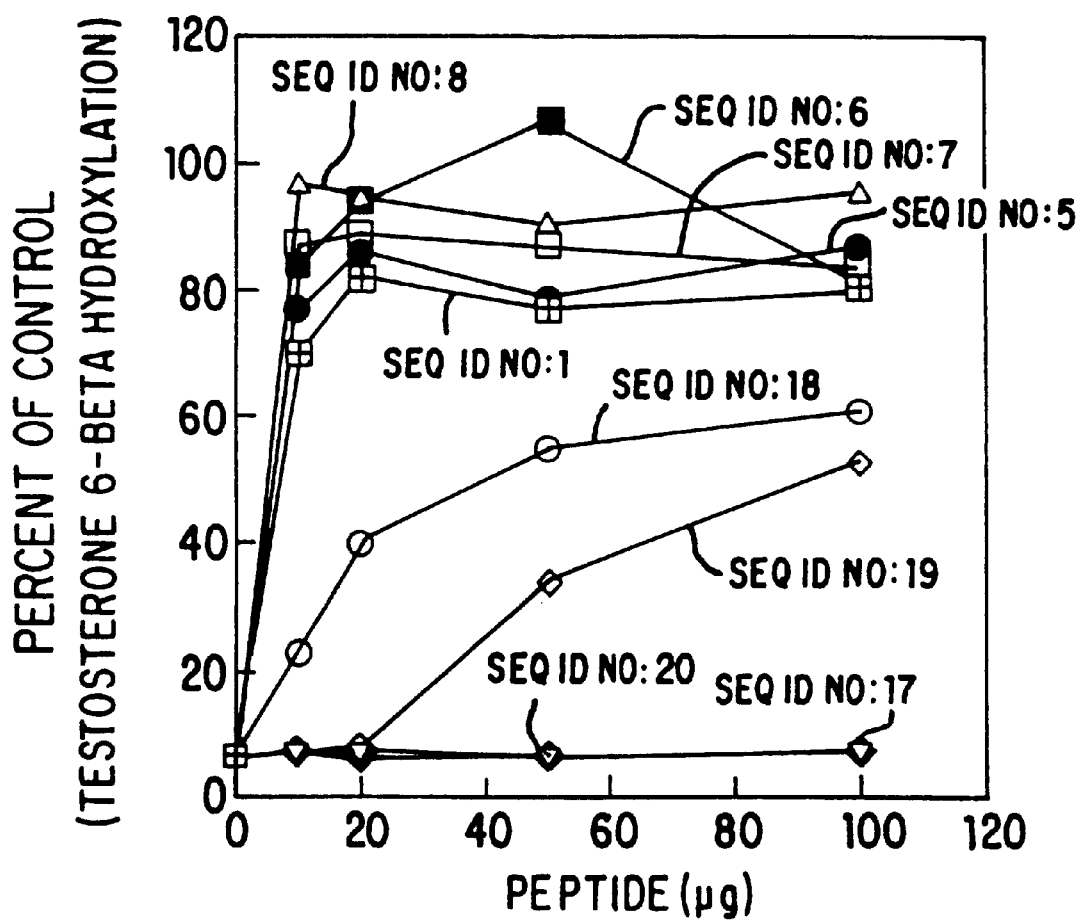
FIG. 8 shows the ability of various peptides (from concentrations up to 100 mg) disclosed as SEQ ID NOS:1, 5, 6, 7, 8, and 17–20 to effect the ability of the inhibitory antibody raised against SEQ ID NO: 1 to inhibit testosterone 6β-hyrdoxylation (as a percent of control).

FIG. 8 shows that SEQ ID NOS:5, 6, and 7 exhibit a similar ability to diminish the inhibitory effect of antibodies raised against SEQ ID NO:1. This data suggests that the inhibitory epitope is at least contained within SEQ ID NO:9.

Figure 9:
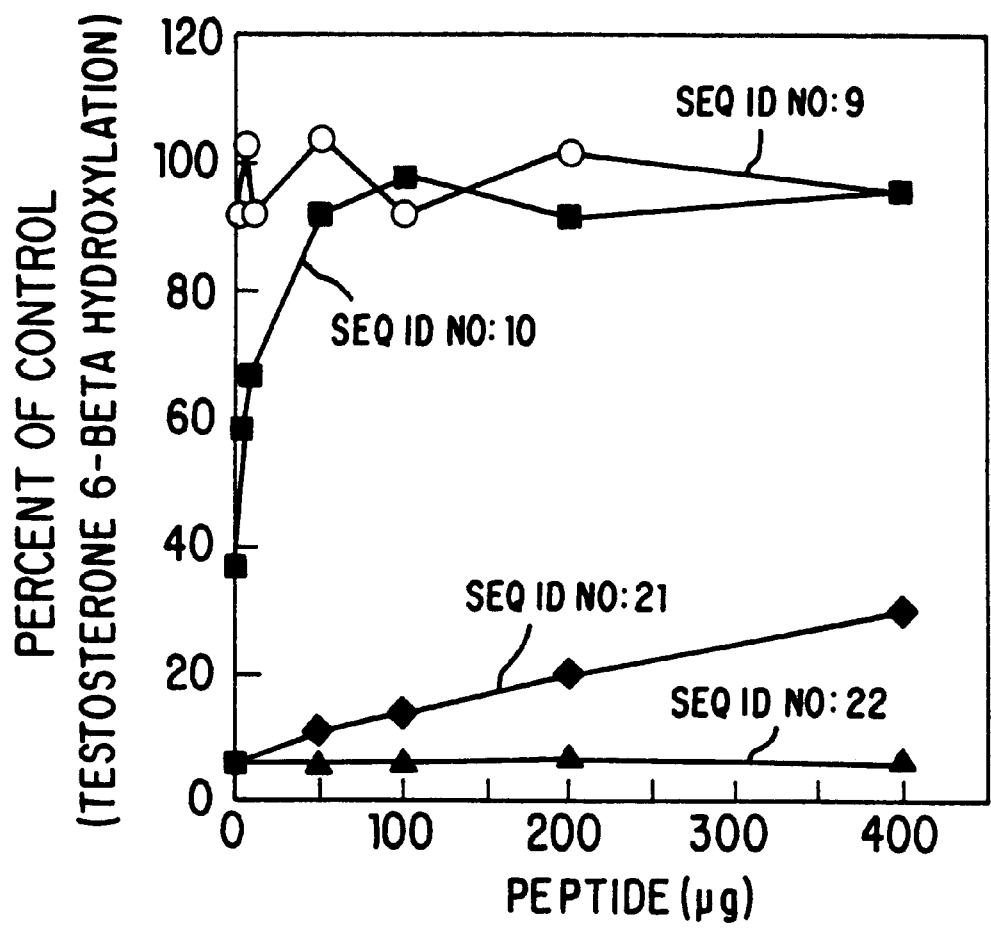
FIG. 9 shows the ability of various peptides (concentrations up to 400 mg) disclosed as SEQ ID NOS:9, 10, 21 and 22 to effect the ability of the inhibitory antibody raised against SEQ ID NO: 1 to inhibit testosterone 6β-hyrdoxylation (as a percent of control).
Figure 10:
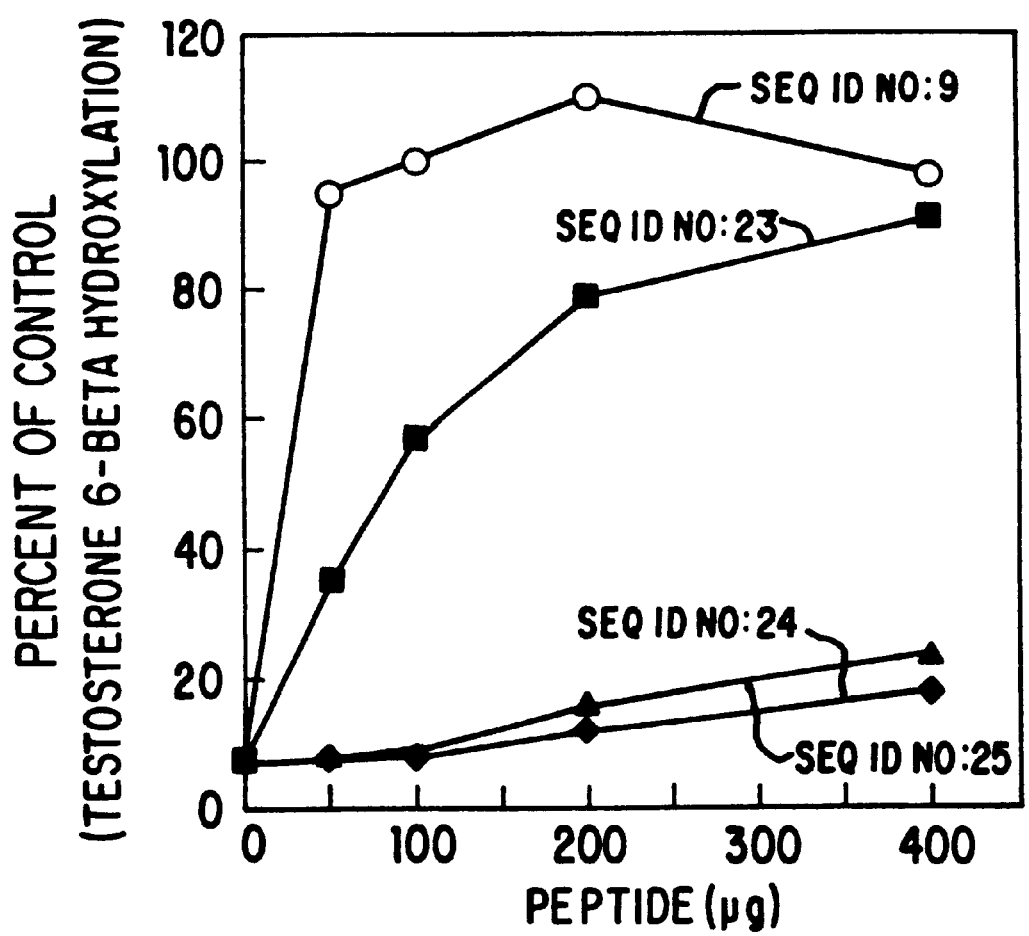
FIG. 10 shows the ability of various peptides (concentrations up to 400 mg) disclosed as SEQ ID NOS:9, 23, 24 and 25 to effect the ability of the inhibitory antibody raised against SEQ ID NO: 1 to inhibit testosterone 6β-hyrdoxylation (as a percent of control).
Figure 11:
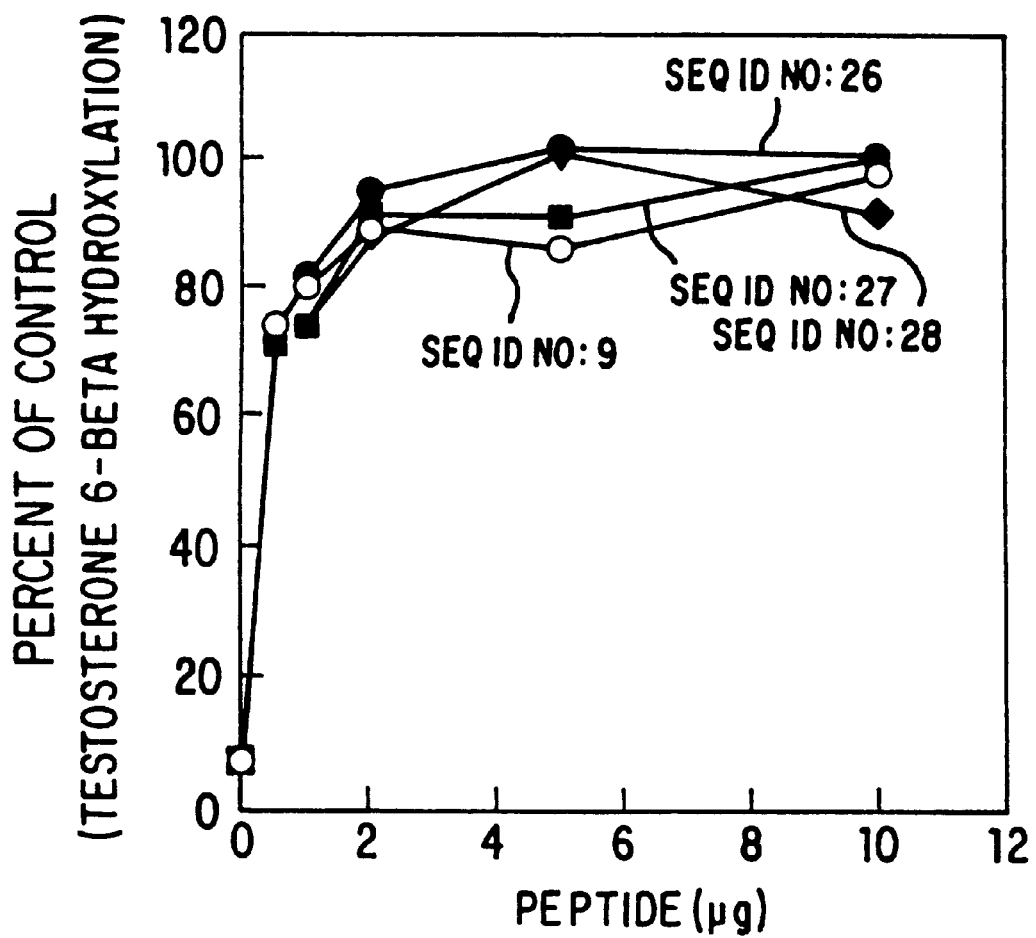
FIG. 11 shows the ability of various amino and/or carboxyl terminal modified peptides (concentrations up to 10 mg) disclosed as SEQ ID NOS:9 and 26–28 to effect the ability of the inhibitory antibody raised against SEQ ID NO: 1 to inhibit testosterone 6β-hyrdoxylation (as a percent of control).

FIG. 9 shows the further delineation of the inhibitory epitope whereby SEQ ID NO:9 and several amino terminus deletions (SEQ ID NOS 10, 21 and 22 were tested for their ability to diminish the inhibitory effect of antibodies raised against SEQ ID NO:1. SEQ ID NOS:9 and 10 were effective in inhibiting the antibodies of the present invention. Therefore, an inhibitory epitope is at least contained within SEQ ID NO:9 or SEQ ID NO:10.

FIG. 10 shows the further delineation of the inhibitory epitope whereby SEQ ID NO:9 and several carboxy terminus deletions (SEQ ID NOS 23, 24 and 25 were tested for their ability to diminish the inhibitory effect of antibodies raised against SEQ ID NO:1. This data shows that an inhibitory epitope exists within the entire SEQ ID NO:9.

FIG. 11 shows the ability of various amino- and/or carboxy-terminus modified peptides (SEQ ID NOS: 26, 27 and 28) to diminish the inhibitory effect of antibodies raised against SEQ ID NO:1. This data shows that the core epitope of SEQ ID NO:9 is effective competing out the effect of the inhibitory antibodies raised against the peptide of SEQ ID NO:1, whereas the free amino and carboxyl groups are not important for the inhibitory epitope since modification of these groups does not affect the ability of the inhibitory antibody raised against SEQ ID NO:1 to inhibit testosterone 6β-hydroxylation.

What is claimed is:

1. Anti-peptide antibody raised against a peptide consisting of the amino acid sequence disclosed as SEQ ID NO:1 which is specific to human CYP3A4 even in the presence of CYP3A5 and inhibits at least about 80% of human CYP3A4 enzyme activity.

2. The anti-peptide antibodies of claim 1 wherein said anti-peptide antibodies inhibit at least about 90% of human CYP3A4 activity.

* * * * *